(12) United States Patent
Backhaus et al.

(10) Patent No.: US 6,210,803 B1
(45) Date of Patent: Apr. 3, 2001

(54) METHOD FOR THE PRODUCTION OF A GRANULATE FOR HEMODIALYSIS

(75) Inventors: Wendelin Backhaus, Weilmünster; Peter Hilgers, Wetzlar; Joachim Manke, Löhnberg; Hamadi El-Ayari, Frankfurt; Werner Liedy, Hochdorf-Assenheim, all of (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/214,078

(22) PCT Filed: Apr. 23, 1998

(86) PCT No.: PCT/EP98/02425

§ 371 Date: Jun. 17, 1999

§ 102(e) Date: Jun. 17, 1999

(87) PCT Pub. No.: WO98/47488

PCT Pub. Date: Oct. 29, 1998

(30) Foreign Application Priority Data

Apr. 24, 1997 (DE) .............................. 197 17 362

(51) Int. Cl.⁷ ...................................... B32B 5/16
(52) U.S. Cl. .............. 428/402; 23/303; 23/304; 23/313 R; 23/293 A
(58) Field of Search .............. 428/402; 23/303, 23/304, 313 R, 293 A; 424/489

(56) References Cited

U.S. PATENT DOCUMENTS

| | | | |
|---|---|---|---|
| 4,451,454 | * 5/1984 | Wong ................................... | 424/127 |
| 4,489,535 | * 12/1984 | Veltman ............................... | 53/431 |
| 4,655,941 | * 4/1987 | Suzuki ................................. | 252/1 |
| 4,756,838 | * 7/1988 | Veltman ............................... | 252/1 |
| 4,834,882 | * 5/1989 | Kataoka et al. ................... | 210/321.6 |
| 4,925,534 | * 5/1990 | Kataoka et al. ..................... | 210/647 |
| 5,071,558 | * 12/1991 | Itoh ..................................... | 210/542 |
| 5,122,516 | * 6/1992 | Watanabe et al. .................... | 514/23 |
| 5,616,248 | * 4/1997 | Schal ................................... | 210/647 |

FOREIGN PATENT DOCUMENTS

| | | |
|---|---|---|
| 0 602 014 A1 | 6/1994 | (EP) . |
| 0 602 921 A1 | 6/1994 | (EP) . |
| 0 613 688 A1 | 9/1994 | (EP) . |
| 06 105 906 | 4/1994 | (JP) . |

* cited by examiner

Primary Examiner—H. Thi Le
(74) Attorney, Agent, or Firm—Kenyon & Kenyon

(57) ABSTRACT

The invention relates to a method for the manufacture of an electrolyte and acetic acid granulate for making a hemodialysis solution, the granulate comprising the electrolytes potassium chloride, calcium chloride and magnesium chloride, and the method comprising preparing the granulate and adding a desired quantity of acetic acid. The granulate, which is easy to process and has free flow capability, is made by crushing the electrolyte salts to a grain size of less than 0.5 mm and subsequently granulating the electrolyte salts in a dry gas atmosphere to a granulate having a grain size of 1 to 10 mm and a pore volume of more than 25 percent by volume. Subsequently, the acetic acid is added to the granulate, preferably by spraying.

35 Claims, 1 Drawing Sheet

METHOD FOR THE PRODUCTION OF A GRANULATE FOR HEMODIALYSIS

FIELD OF THE INVENTION

The invention relates to a method for the manufacture of a granulate for the supply of a hemodialysis solution containing bicarbonate and the electrolytes required for hemodialysis.

BACKGROUND OF THE INVENTION

Dialysis as a medical therapy for patients with an impaired or lost renal function has been described extensively together with its varied technical aspects in the literature.

For hemodialysis, around 120 to 180 liters of hemodialysis solution are required for one treatment. This is a watery solution, typically of the following composition:

| Component | Concentration range | Typical concentration |
|---|---|---|
| $Na^+$ | 125–150 mmol/ltr. | 128 mmol/ltr. |
| $K^+$ | 0–5 mmol/ltr. | 2 mmol/ltr. |
| $Ca^{++}$ | 0.3–2.5 mmol/ltr. | 1.5 mmol/ltr. |
| $Mg^{++}$ | 0–1.5 mmol/ltr. | 0.5 mmol/ltr. |
| $Cl^-$ | 92–120 mmol/ltr. | 110 mmol/ltr. |
| $HCO_3^-$ | 30–40 mmol/ltr. | 32 mmol/ltr. |
| Acetate | 1.5–4 mmol/ltr. | 3 mmol/ltr. |
| Glucose | 0–3 g/ltr. | 1 g/ltr. |

The hemodialysis solution is manufactured in a dialysis unit by mixing electrolyte concentrates with pure water. The composition here must meet the physiological requirements as the hemodialysis solution comes into contact with the patient's blood through a semipermeable membrane.

The problems involved in preparing a suitable, physiological composition of hemodialysis solution are presented, for example, in detail in the book "Replacement of renal function by dialysis" (by W. Drukker, F M Parsons, J. F. Maher, Publishers: Martinus Mijhoff Medical Division Den Haag) in the main section "The composition of dialysis fluid" (authors: F. M. Parsons, A. M. Davison).

It is known and is also seen from this publication that the composition of the hemodialysis solution has to be adapted to the specific needs of the individual patient.

As 120 to 180 liters of hemodialysis solution are required for a treatment of four to six hours, it is appropriate to prepare the hemodialysis solution at the place of application.

Dialysis units have been developed where the hemodialysis solution is manufactured continuously or in small partial quantities by means of automatic dosage devices. This is normally done in such a manner that a ready-made fluid concentrate is diluted with pure water in a certain volumetric ratio (the standard ratio being one volume unit of concentrate to 35 parts of the finished solution). Fluid concentrates in a variety of composition versions are available for this method.

The application of the dialysis concentrates at the units is performed in a number of different ways. One standard technique is that of a so-called central supply. Here, a fairly large number of dialysis units of a center are supplied with concentrate via a pipe system from one central location.

One serious disadvantage of central concentrate supply is, however, that it is not possible to have a specific adaptation of the composition to the needs of the individual dialysis patient as only one concentrate type at a time can be distributed via a concentrate supply network.

The use of concentrate canisters at the individual dialysis unit is the most widespread application. The unit is then connected to a supply line through which the pure water (prepared and with controlled quality) is supplied. The concentrate is made available at the dialysis unit in commercial canisters (e.g. 6 or 10 liters) and taken up by the unit through a device led into the canister.

One big advantage of this method is that a particularly suitable concentrate can be selected for the treatment of each individual patient. Such an adaptation, known under the name of "individualization", is generally recognized as being important.

The use of concentrates in canisters represents a substantial strain on the persons working in dialysis wards as the concentrate canisters weight up to 10 kg. The stocking of different concentrates in such large canisters requires a great deal of effort. For a dialysis ward with 20 treatment sites, the typical stock quantity for one week will be on the order of 200 to 300 canisters. Residues of concentrates not fully used up, which remain in the canister after the treatment, should not be used again for a number of reasons. The disposal of these residues, which may well make up to 30 per cent of the actual quantity required, represents a substantial pollution of the environment. The used, empty canisters, normally canisters made of high-quality thermoplastics, cannot be reused for the same purpose according to the state of the art and when taking economic and organizational criteria into account. Returning them into the raw material cycle by means of recycling is, however, not a very economic process, either.

In addition, the hemodialysis solution containing bicarbonate cannot be made from just a single solution concentrate. Concentrates that contain $Mg^{++}$ and/or $Ca^{++}$ are only stable without bicarbonate, because the presence of bicarbonate precipitation of carbonate to occur.

Bicarbonate dialysis therefore requires the use of at least two separate concentrates, namely a bicarbonate concentrate, usually in the form of a pure sodium bicarbonate solution, and a concentrate of the other components of the solution, this latter concentrate normally bearing the name "acid bicarbonate hemodialysis concentrate". The hemodialysis units intended for bicarbonate dialysis must be equipped with two separate dosage proportion devices for these two concentrates.

The risk of precipitation of carbonates only occurs with this method after the components have been mixed. However, this is of only minor significance in hemodialysis as the length of time the mixed hemodialysis solution spends in the line system of the dialysis unit, including the dialyzer, is only on the order of one minute.

Another problem in bicarbonate dialysis is that the commercial bicarbonate solution is not autosterile. The bicarbonate concentrate must therefore be produced in a sterile form with increased care and be stored in sterile form in suitable containers until use.

The fluid concentrates described above contain up to 80% water and are therefore of great disadvantage from a logistical point of view.

In addition to the fluid concentrates, there is the possibility of manufacturing the concentrates on site from the raw salts. The salts must then be dissolved in pure water prior to the treatment. Their manufacture requires great care and is very time consuming.

An alternative is provided by granulates which consist exclusively of the substances required for dialysis. For example, bicarbonate granulates are already known as a first, base concentrate, with the rest of the total solution components consisting of the electrolytes ($Mg^{2+}$, $Ca^{2+}$, $K^+$ $Na^+$) and a physiologically compatible acid being comprised in a second concentrate. It is also already known to take the sodium chloride portion out of the acid electrolyte portion and to dispense it as a third concentrate for an individual patient treatment. This has already been described in EP 0 613 688.

For example, it is also already known from EP 0 602 014 A1 to make the electrolyte portions available in granulate form. Here, it has already been described that the desired acetic acid quantity is added to this granulate of the electrolytes. However, according to the state of the art, there is the risk that the granulates manufactured there lose their free-flowing capability due to the absorption of the acetic acid.

OBJECTS OF THE INVENTION

It is the object of the invention to provide a method for the manufacture of a granulate of the electrolytes required for the provision of a hemodialysis solution containing bicarbonate for hemodialysis together with the desired quantity of acetic acid in a form in which the granulate represents loose material that is easy to process and capable of free-flow.

This object is achieved by a method for the manufacture of the desired granulate according to the present invention wherein, the salts are first taken in a grain size of less than 0.5 mm and then granulated in a dry gas atmosphere to a grain size of 1 to 10 mm, advantageously of around 2 mm, with a pore volume being generated in the granulate of more than 25 percent by volume. Then the acetic acid is sprayed onto the granulate in a vacuum. By means of these combined process steps, a pore volume of more than 25% is generated, with it being possible to absorb the total required quantity of acetic acid in the pores of this granulate. In addition, in the solution in accordance with the invention, the acetic acid that is contained in the concentrates of the prior art is not include in the granulation process.

Preferably, a granulate is manufactured which possesses a pore volume of between 37 and 60 percent by volume. With such a high pore volume, it is easily possible to have between 15 and 35 percent by weight of acetic acid per total electrolyte quantity, ideally between 18 and 20 percent by weight.

Although different granulation methods can be used, it has been found to be particularly advantageous to use fluidized beds to manufacture the granulates. In particular, the following two known techniques can be used:

Granulation of solids usually presented as a fine powder to larger granulates by the jet spraying of solvent and the drying of this solvent in the fluidized bed.

Manufacture of granulates beginning with a presentation of solid particles by jet spraying of the solids dissolved in a solvent and the drying of this solvent in the fluidized bed.

The preferred solvent in accordance with the invention is polar, water being particularly preferred.

Both methods are suitable for the manufacture of granulates with the desired pore structure which allow a simple absorption of the acetic acid in its pore volume.

Of particular advantage is the combination of the two method versions, with both versions being able to be performed in a fluidized bed. By setting the portions of different components of the "presentation" and the "solids jet sprayed in solution", the properties of the pore system can be optimized by taking the recipe into account.

It has in particular been found to be advantageous to jet spray those components in dissolved for that clearly differ in their particle size distribution from the other starting materials. In this way, separation phenomena and associated inhomogeneities of the granulate can be avoided. The thorough drying (final or residual drying) can also be performed in the fluidized bed to reduce mechanical stress on the granulates or in a shaft drier or in another drier.

Thanks to the method management in accordance with the invention, a pore system with special properties can be created in the granulate. Here, influence is first taken on the pore radius distribution, with these depending on the radius of the particles used. In this way, deliberately fine pores can be created on the inside and crude pores in the outside region. The fine pores in the inside region provide good uptake of the acetic acid sucking in of the acetic acid due to the effective capillary force while the crude pores in the outside region lead to a good free flow capability of the granulates. In addition, the properties of the inner surfaces can be specifically influenced, with the surface tension and/or the interfacial tension between the solid surface and the fluid acetic acid capable of being influenced by the fact that one or more pre-determined components can be applied to the inner surface via the solids jet sprayed on in solution to improve the wetting behavior of the acetic acid.

The application of the acetic acid, which is advantageously carried out in vacuum, can, for example, be jet sprayed on in a mechanically gentle mixer or, however, after the pouring of the granulates into a container.

The method according to the invention results in a granulate for use in making a hemodialysis solution comprising electrolytes and fluid acetic acid, wherein the granulate has a grain size of at least 1 mm, the granulate has pores making up at least 25 percent of the granulate volume, the granulate has absorbed at least 18 percent by weight acetic acid, and the granulate has free flow capability.

A granulate in accordance with the invention is produced from claim 14.

DETAILED DESCRIPTION OF THE PREFERRED EMBODIMENT

Figure 1:
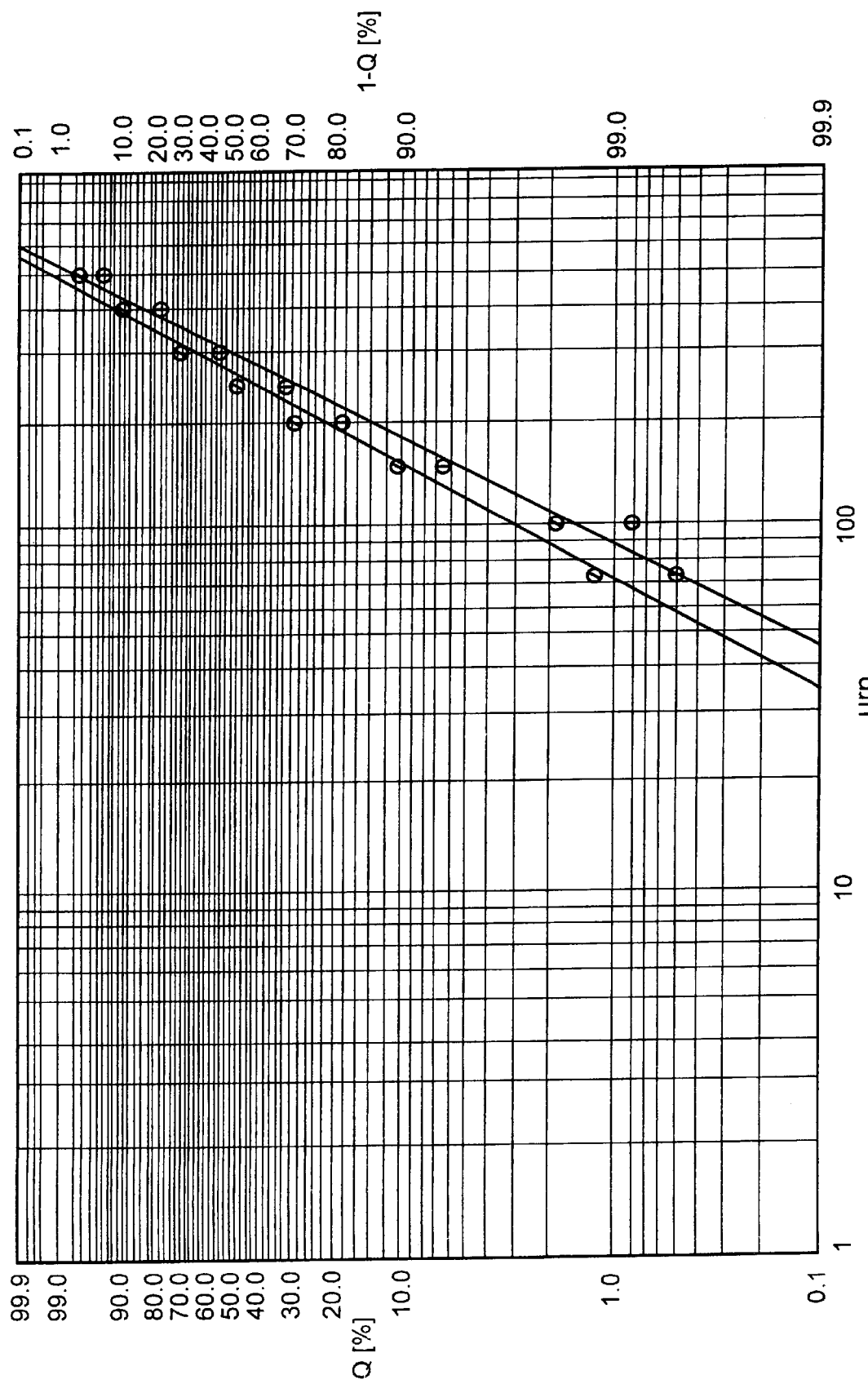
FIG. 1 illustrates the grain size distribution of a granulate prepared according to the invention.

Further details and advantages of the invention are presented below by means of examples which describe preferred embodiments of the method in accordance with the invention.

The typical composition of the granulate manufactured by the method in accordance with the invention is produced as follows:

$CaCl_2$: 50 percent by weight

KCl: 15 to 35 percent by weight $MgCl_2$: 15 to 35 percent by weight

Acetic acid: 35 percent by weight mass load with reference to the total salt mass; and Optionally:

Glucose: 0 to twice the weight portion of the total salt mass.

The exemplary method procedure is as follows:

1. Weigh out the components of salt, water to be sprayed and, if required, glucose;
2. Heat the spray fluidized bed granulator to an operating temperature of around 80° C.;

3. Grind the three salts (MgCl$_2$, CaCl$_2$ and KCl) to a grain size of ≦0.5 mm. The salts should advantageously be crushed individually or separately from one another as otherwise Carnallit formation may occur;
4. Add the three salts to the spray fluidized bed granulator;
5. Set the heating gas volume flow so that a uniform fluidized bed is created;
6. Heat the fluidized bed to operating temperature and simultaneously homogenize the salt mixture;
7. Start the spray process by introducing compressed air or other gases and the spray medium into the fluidized bed through a two-component nozzle. The fluid introduced dissolves the surface of the salt particles so that these gradually stick to one another while forming fluid bridges. The fluid introduced is dried during this process, with solid bridges being created;
8. Adjustment of the heating gas volume flow during the volume and weight growth of the spongy granulates which are formed. The granulate growth develops best when at the start a lot of spray medium is introduced and at the end rather less. The temperature must be adjusted;
9. Reduce the heating gas volume flow after the granulates have reached the desired size in order to keep the mechanical stress during the subsequent drying as low as possible;
10. Remove the finished granulates from the spray fluidized bed granulator to the exclusion of air as the granulates are highly hygroscopic;
11. Acetic acid in fluid form is introduced to the pore system of the granulates, for example in a drum mixer or a rotation vacuum evaporator, preferably in vacuum;
12. The finished individual concentrate granulate is poured to the exclusion of ambient air into a bag which should be as resistant to diffusion as possible or optionally into a cartridge.

Below, the trial series to determine the absorption capability of the granulate in accordance with the invention for acetic acid is reproduced. To determine how much acetic acid can be absorbed by the granulate in accordance with the invention, acetic acid is applied to the granulate using a Rotavapor (manufacturers: Büichi, Switzerland, Büchi B 153) at a pressure of 60 mbar (absolute). Then the properties of the granulate are examined.

In the measurement, 100 g of the granulate in accordance with the invention is poured into a spherical vessel with a volume of approximately 5 liters. The vessel is then evacuated using a vacuum pump to a pressure of 60 mbar (absolute). The acetic acid is washed over the granulate using a nozzle (0.1 mm) while the glass sphere rotates.

The granulate in accordance with the invention is first examined using an air-jet sieve (Air jet sieve 200 LS-N from Hosokawa Alpine AG, Augsburg) as to its grain size distribution. The focus of the distribution was at 350 μm (see FIG. 1). The granulate is comprised of 40% KCl, 30% MgCl$_2$ and 30% CaCl$_2$.

Using the Rotavapor, different amounts of acetic acid were added to the granulate. The quality criterion used was the free flow capability of the granulate with the acetic acid. The results are shown in the following Table 1.

| Granulate quantity [g] | Acetic acid quantity [g] | Flow capability |
| --- | --- | --- |
| 100 | 2 | Yes |
| 100 | 4 | Yes |
| 100 | 6 | Yes |
| 100 | 8 | Yes |
| 100 | 10 | Yes |
| 100 | 12 | Yes |
| 100 | 14 | Yes |
| 100 | 16 | Yes |
| 100 | 18 | Yes |
| 100 | 20 | No |

It can be seen from Table 1 that the granulate in accordance with the invention is capable of absorbing up to 18 percent by weight of acetic acid. If the size of the granulates is increased, an increase in the acetic acid capacity can also be expected.

The grain size distribution of the granulate is shown in FIG. 1.

What is claimed is:

1. A method of manufacturing an electrolyte granulate in combination with acetic acid useful for making a dialysis solution, comprising the steps of:
    (a) providing electrolyte salts having a grain size of less than or equal to 0.5 mm;
    (b) granulating the electrolyte salts into a granulate having a grain size from 1 to 10 mm and a pore volume of greater than about 25 percent; and
    (c) applying acetic acid to the granulate.

2. The method of claim 1, wherein the electrolytes comprise salts of potassium chloride (KCl), calcium chloride (CaCl$_2$) and magnesium chloride (MgCl$_2$).

3. The method of claim 2, further comprising the step of grinding the electrolyte salts into particles of less than or equal to 0.5 mm.

4. The method of claim 3, wherein each of the electrolyte salts is ground separately.

5. The method of claim 2, wherein the electrolyte salts are granulated into a granulate using a fluidized bed by the steps of:
    (a) jet spraying a solvent onto the electrolyte salts in the fluidized bed; and
    (b) drying the solvent.

6. The method of claim 5, wherein the solvent is dried in vacuum.

7. The method of claim 5, wherein the solvent is water.

8. The method of claim 5, wherein drying of any residual solvent is carried out in the fluidized bed.

9. The method of claim 5, wherein the drying of any residual solvent is carried out in a dryer selected from the group consisting of a shaft drier and a belt drier.

10. The method of claim 5, wherein the granulate is prevented from contacting moisture after production in the fluidized bed.

11. The method of claim 5, wherein the granulate is prevented from contacting air after production in the fluidized bed.

12. The method of claim 2, wherein the electrolyte salts are granulated into a granulate using a fluidized bed by the steps of:
    (a) providing electrolyte salt particles in the fluidized bed;
    (b) jet spraying the electrolytes dissolved in a solvent onto the particles provided in the fluidized bed; and
    (c) drying the solvent.

13. The method of claim 2, wherein the electrolyte salts are granulated into a granulate using a fluidized bed by the steps of:
   (a) providing particles of at least one of the electrolyte salts in the fluidized bed;
   (b) jet spraying the other electrolyte salts dissolved in a solvent onto the electrolyte salts provided in the fluidized bed; and
   (c) drying the solvent.

14. The method of claim 2, wherein the electrolyte granulate and acetic acid combination comprises:
   50 percent by weight $CaCl_2$;
   15 to 35 percent by weight KCl;
   15 to 35 percent by weight $MgCl_2$; and
   35 percent by weight acetic acid as compared to the salt mass.

15. The method of claim 2, wherein the electrolyte granulate and acetic acid combination comprises 15 to 35 percent by weight acetic acid as compared to the salt mass.

16. The method of claim 2, wherein the electrolyte granulate and acetic acid combination comprises 18 to 20 percent by weight acetic acid as compared to the salt mass.

17. The method of claim 1, wherein the pore volume of the granulate is between about 37 and about 60 percent.

18. The method of claim 1, wherein fine pores are generated on the inside of the electrolyte granulate and larger pores are generated on the outside of the granulate.

19. The method of claim 1, wherein the acetic acid is jet sprayed onto the granulate.

20. The method of claim 19, wherein the acetic acid is sprayed onto the granulate in vacuum.

21. The method of claim 19, wherein the acetic acid is sprayed onto the granulate in a mechanical mixer.

22. The method of claim 1, wherein glucose is granulated with the electrolyte salts.

23. The method of claim 22, wherein the electrolyte granulate and acetic acid combination further comprises glucose in an amount of up to twice the weight proportion of the total electrolyte mass.

24. The method of claim 1, wherein the granulate produced has a grain size of about 2 mm.

25. A granulate for use in making a hemodialysis solution comprising electrolytes and acetic acid, wherein:
   the granulate has a grain size of at least 1 mm;
   the granulate has pores making up at least 25 percent of the granulate volume;
   the granulate has absorbed at least 15 percent by weight acetic acid; and
   the granulate has free flow capability.

26. The granulate of claim 25, wherein the electrolytes making up the granulate comprise potassium chloride, calcium chloride and magnesium chloride.

27. The granulate of claim 26, wherein the granulate comprises:
   50 percent by weight $CaCl_2$;
   15 to 35 percent by weight KCL;
   15 to 35 percent by weight $MgCl_2$; and
   35 percent by weight acetic acid.

28. The granulate of claim 26, wherein the granulate comprises:
   30 percent by weight $CaCl_2$;
   40 percent by weight KCl;
   30 percent by weight $MgCl_2$; and
   18 percent by weight acetic acid.

29. The granulate of claim 25, further comprising glucose.

30. The granulate of claim 29, wherein the glucose is included at up to twice the weight proportion of the total electrolyte mass.

31. The granulate of claim 25, wherein the granulate has a grain size of from 1 to 10 mm.

32. The granulate of claim 25, wherein the granulate has a grain size of 2 mm.

33. The granulate of claim 25, wherein the pores make up from 37 to 60 percent of the granulate volume.

34. The granulate of claim 25, wherein the granulate has absorbed 15 to 35 percent by weight acetic acid.

35. The granulate of claim 25, wherein the granulate has adsorbed 18 to 20 percent by weight acetic acid.

* * * * *

UNITED STATES PATENT AND TRADEMARK OFFICE
CERTIFICATE OF CORRECTION

PATENT NO.  : 6,210,803 B1
DATED       : April 3, 2001
INVENTOR(S) : Wendelin Backhaus et al.

Page 1 of 1

It is certified that error appears in the above-identified patent and that said Letters Patent is hereby corrected as shown below:

Column 2,
Line 35, after "(bicar-)bonate" and before "precipitation", add -- may cause --;

Column 3,
Lines 26 and 27, "invention wherein", should be changed to --invention, wherein --;
Line 38, "include" should be changed to -- including --;

Column 4,
Line 2, "for" should be changed to -- form --;
Line 16, delete "sucking in of the acetic acid";
Lines 37 and 38, delete "A granulate in accordance with the invention is produced from claim 14."

Signed and Sealed this

Twenty-eighth Day of May, 2002

Attest:

Attesting Officer

JAMES E. ROGAN
Director of the United States Patent and Trademark Office